United States Patent [19]

Sajó et al.

[11] Patent Number: 4,491,633

[45] Date of Patent: Jan. 1, 1985

[54] METHOD FOR THE FAST CALORIMETRIC QUALIFICATION OF PUZZOULAN MATERIALS

[75] Inventors: István Sajó; György Vámos; Miklós Ürmössy; Barbara Sipos née Kaveczka; Éva Zemplén née Papp; Éva Borsovszky, all of Budapest; László Barta, Vécs, all of Hungary

[73] Assignee: Energiagazdalkodasi Intezet, Budapest, Hungary

[21] Appl. No.: 430,239

[22] Filed: Sep. 30, 1982

[30] Foreign Application Priority Data

Oct. 14, 1981 [HU] Hungary ............................. 2955/81

[51] Int. Cl.$^3$ ............................................. G01N 25/48
[52] U.S. Cl. ................................ 436/147; 106/DIG. 1; 374/31
[58] Field of Search ................... 106/DIG. 1; 436/147, 436/72, 2, 100, 183, 124; 374/31

[56] References Cited

U.S. PATENT DOCUMENTS 3,578,405  5/1971  Woodle ................................. 374/31

OTHER PUBLICATIONS

*Heat of Hydration of Cement by Simple Apparatus*, by William Lerch, Engineering News-Record, Oct. 25, 1934.
Use of Pozzolans in Concrete, by Raymond E. Davis, Journal of the American Concrete Institute, Jan. 1950, Title #46-24.
The Use of Thermal Power Station Pulverized Fuel Ash in the Manufacture of Cement in Hungary, by Robert Kovach, delivered orally Nov. 1970 at a Symposium at Ankara, Turkey.

*Primary Examiner*—Barry S. Richman
*Assistant Examiner*—Joseph P. Carrier
*Attorney, Agent, or Firm*—Burgess, Ryan & Wayne

[57] ABSTRACT

A qualification method which enables a fast, exact and numerical determination of puzzoulana-properties of solid materials and thus a short evaluation of said solid materials from the point of view of industrial usability.

According to this method the puzzoulana-properties and activity of solid materials can be defined by a single figure as a result of their chemical and physical properties. The material to be analyzed is brought together with fluoride ions in an acidic medium in a system having constant heat capacity and the change of the heat quantity is measured and evaluated in the initial, suitable linear, phase of the resulting reaction. The time function of the change of the heat quantity of the system is converted into a change of voltage and the rise of this curve is determined advantageously in the linear section. Advantageously the change of the heat quantity of the system is measured within less than 30 seconds, favorably at about the 20th second. This measured result is evaluated by using a constant value being characteristic of said material and programmed in a computer and the activity of e.g. fly ash is given in a dimension of mg CaO/g fly ash.

5 Claims, No Drawings

METHOD FOR THE FAST CALORIMETRIC QUALIFICATION OF PUZZOULAN MATERIALS

The invention relates to a new method for the fast qualification of solid materials, mainly of puzzoulanas. The aim of this qualification is to determine or predict the industrial usability of these materials.

It is very important in the practice to determine in advance some substantial properties of basic industrial raw materials used for manufacturing some industrial products since in the knowledge of these properties one can determine the optimal conditions of manufacturing. For the most part these basic raw materials are minerals or other substances of mineral origin and great quantities of these materials with a great variety of chemical and physical properties are used in certain branches of industry. Preliminary qualification of basic raw materials the whole structure according to the classic analytical methods while the methods without destruction are used for determination of physical properties in most instances.

However, very often such characteristics have to be determined in practical cases which depend on both the chemical and physical properties of the materials and the interaction of these properties can not be defined numerically at all or only by very complicated methods. So the actual properties which are characteristic of certain materials, e.g. the reactivity, can be only very circumstantially determined by conventional methods, in the case of reactions between solid materials. The behaviour of a certain material is determined by many factors in a given reaction not only by its chemical composition but inter alia by the specific surface, the availability of its surface, the ratio between the crystalline and amorphous phases, the size and porosity of the particles, the moistening capacity, etc. as well.

The above statements are especially true in the case of the preliminary qualification of puzzoulanas and other substances of mineral origin or milling products and mixtures thereof. Namely, to determine such properties of these materials which are decisive from the point of view of their industrial applicability is a typical task that can be solved by conventional methods only with great loss of time and under enormous difficulties. For example, the requirements raised to one type of puzzoulanas, i.e. fly ash, can be very different depending on the field of utilization. On the basis of research and experience made so far, it can be generally said that fly ash of coarse particle size and of given moisture content are suitable for building a resistant bank whereas those of fine particle size and which are quite dry, are the best as concrete additives. But one of the most important characteristics of fly ash for as concrete and mortar or other binding material additives is the so-called hydraulic activity. This expression refers to the property of fly ash that its soluble constitutents are able to react with calcium hydroxide originating from the hydratation of binding materials, e.g. concrete, or added into the system by an other way and as a result of this reaction, secondary hydrated phases, mostly calcium silicate hydrates, form. These materials are similar to hydrated products of concrete and responsible for the binding. The rate of these reactions depends to a great extent on the quantity of reacting soluble constituents, i.e. it depends on the chemical composition of the material, the value of its specific surface and the ratio of vitreous phases, respectively.

So far, however, there is no standardized analytical method for such a qualification of fly ash. As the hydraulic activity of fly ash depends on its above-mentioned chemical and physical properties, first of all, the so-called lime adsorption method (described in a Soviet standard referred to in the present specification as GOST) is used for the qualification in the practice. But this means practically that the qualification of a waste material, in the present case that of fly ash, can be carried out only after the time prescribed in this standard, i.e. after 28 days. One can rank the value of a fly ash as a puzzoulana used in a subsequent production process only after this period. Even in the case of advantageous results of the above analysis, one has to reckon with the fact that the physical properties of fly ash could undergo a complete change in comparison with its initial stage during the period of analysis or it could be mixed with other fly ash of different quality in the course of its storage.

It is obvious from the foregoing that the known methods for the determination of the hydraulic activity of puzzoulanas have a great drawback in the sense that an opinion about their best usability can be only formed with a very great time-lag, i.e. after 28 days, in practice. Moreover, these methods are rather ponderous as well and only the ability of lime adsorption of the material in question is determined essentially by a chemical analysis. According to the prior art, in our best knowledge, there is no more developed method than the above-mentioned one for the determination of the hydraulic activity of puzzoulanas and for the qualification of these materials from the point of view of industrial usability.

Thus, the aim of the invention is to develop a method for qualification of the properties of puzzoulanas through a fast, exact and numerical determination and thus making it possible to evaluate the solid materials in question in a short time. With this qualification method, it is intended to determine the properties of certain materials, dusty products or milled products which are jointly typical for their chemical and physical properties. By this means, on the one hand, we want to render possible the fast measurement of the suitability of certain materials for given technologies and, on the other hand, the qualifying control of pre-treating technologies comprising comminution and grinding.

Our invention is based on the unexpected recognition that it is possible to define the puzzoulana-property and activity of solid materials, first of all of puzzoulanas, from the point of view of industrial usability, by a single figure when, in a system of constant heat capacity, the material to be examined is brought together with fluoride ions in an acidic medium, whereafter, during the reaction taking place in this system, the change of heat quantity is measured and evaluated in the initial, preferably approximately linear, phase. The degree of the change of the heat quantity is measured in the initial, preferably approximately linear, phase of the reaction, most preferably within less than 30 seconds, e.g. at about the 20th second, and by converting the time function of the change of the heat quantity into a change of voltage, the rise of this latter curve is determined which is jointly characteristic for the above-mentioned chemical and physical properties of the material. According to a preferred embodiment of the present invention, a usual computer attached to the above-described thermometric analyser system provides these measured and calculated data directly as mg of adsorbed CaO/g fly ash by using a constant, programmed in advance, in comparison to the lime adsorption by GOST. Naturally, the method of the invention can be performed also with graphic evaluation of the results obtained through the change of the heat quantity and measured by thermometric way, i.e. by reckoning the rise of curve of the linear section and proportioning these data with a standard method, without the use of a previously programmed computer, although in such a manner, this method becomes slower and more difficult. (For the sake of safety we would remark that the type of the computer is by no means critical from the point of view of the present invention.) It is possible to take into account longer or shorter periods of the change of the heat quantity for the evaluation but in our opinion, it is suitable to take a period of about 20 seconds, in the case of Hungarian fly ash because the determination of the activity and the qualification of the products seem to be the most precise at about this moment. In any case, for the sake of authenticity, it is favourable to carry out the measurement according to the method of the invention in the linear section of the time function of the change of the heat quantity.

The following examples are given for illustrating the method according to our invention without limiting, however, the scope of the invention.

EXAMPLE 1

From an average sample of fly ash originating from the steam power station at Pécs (Hungary), an quantity of 3 g is added to 200.0 ml of a 5% aqueous hydrochloric acid solution under continuous stirring. The formed aqueous slurry is brought into the measuring cell of a thermometric titration apparatus. After thermostating during 5 minutes, the slurry is titrated for 1 minute by adding 40% aqueous hydrogen fluoride solution in excess under continuous stirring. During this time, the temperature change is determined and the increase of the heat quantity measured in the 20th second is determined by computer evaluation as an activity value. This value was 40 mg CaO/g fly ash.

By performing the titration of the same average sample of fly ash with an aqueous calcium hydroxide solution according to the GOST, the lime adsorption value of the 28th day is 39 mg CaO/g fly ash after summarizing the values of each day.

After qualifying the fly ash according to the method of the invention, it was used directly in a 1:4 mixture of lime and fly ash for building an agricultural road in the county Tolna (Hungary), where the contractor has asked for the mixture of lime and fly ash as binding material in place of cement. Because the fly ash could not be already analysed by the standard method in due time, the fly ash was qualified by the method of the invention.

This fast use resulted in considerable savings in the building of a road of 2.1 km length.

EXAMPLE 2

A possibility arose in relation to the fly ash originating from the steam power station Gagarin (county Heves, Hungary), that it can be added to a cement when its activity is greater than 70 mg CaO/g fly ash. In this case, it is not necessary to mill the fly ash and the cement together. So, at intervals of 30 minutes, samples were taken from the fly ash continuously leaving the power station and these samples were measured and evaluated in the manner described in Example 1. As the preparation of the sample and the analysis took only some minutes and the calculation of the activity took only a few seconds, it was possible to take steps continuously so that the fly ash could be gathered in a silo when its activity was greater than 70 mg CaO/g fly ash (with a permissible deviation of ±10%) and the fly ash could be directed to a slurry area when its activity was under this limit. It was possible to send such charges of fly ash into the silo so that the average activity of fly ash was 94 mg CaO/g and this fly ash could be directly available for cement production. By doing so, about 19 kWh of electric energy/t cement could be saved.

Afterwards, making the titration by GOST from the average sample of gathered fly ash, a 91 mg CaO/g value of lime adsorption activity for the 28th day could be measured.

The advantages of the method according to the present invention can be summarized as follows:

in a few minutes of sample-preparing and in a very short time, generally within less than 30 seconds, of analysis such a measuring result, characterized only with a single figure for the puzzoulana-activity of a material, is obtained which depends on the chemical and mineralogical composition as well as on the physical properties of this solid material such as the specific surface, the rate of crystalline and amorphous phases, the size of the particles, the porosity, the moistening capacity, etc., the analysed material can be qualified at once practically in the very moment of its formation, from the point of view how and in which ratio is it possible to use it as a raw material in a manufacturing process or for this purpose, materials of the same activity can be gathered and stored together, in general, materials considered otherwise as a waste, e.g. fly ash, becomes useful as a raw material of exactly classified quality.

What we claim is:

1. A method for the fast determination of puzzoulan activity of solid materials, which comprises:
    (a) providing a measured quantity of a solid material of which the puzzoulan activity is to be determined;
    (b) reacting the material with a measured quantity of an aqueous solution of a strong mineral acid, said measured quantity of solution providing a stoichiometric excess of strong mineral acid for reaction with the material to form a reacted acid suspension;
    (c) reacting the reacted acid suspension with fluoride ions in an acidic medium in a system of constant heat capacity; and
    (d) measuring the amount of heat generated during the initial, approximately linear, phase of the reaction with the fluoride ions, whereby the puzzoulan activity is determined as a function of the measurements.

2. A method of claim 1, wherein the rate of heat generation in said system as a result of the fluoride ion reaction is converted into a change of voltage which voltage change forms a curve with a linear part and the slope of the linear part of the curve is determined as a measurement of the puzzoulan activity of the solid material.

3. A method of claim 1 or 2, wherein the measured amount of heat generated is compared to a standard value characteristic of said solid material whereby a relative puzzoulan activity of the material is determined.

4. A method of claim 1 or 2 wherein the amount of heat generated by said system is determined during the initial phase of the reaction with the fluoride ions, within less than 30 seconds after the reaction with the fluoride ions has begun.

5. The method of claim 4 wherein the value of the amount of heat generated is determined at about the 20th second after the reaction with the fluoride ions has begun.

* * * * *